United States Patent
Smith, Jr. et al.

(10) Patent No.: US 9,746,432 B2
(45) Date of Patent: Aug. 29, 2017

(54) SPACER ACCESSORY FOR XRF HANDHELD ANALYZERS

(71) Applicants: Kenneth Lee Smith, Jr., Winchester, MA (US); Ted Michael Shields, Arlington, MA (US)

(72) Inventors: Kenneth Lee Smith, Jr., Winchester, MA (US); Ted Michael Shields, Arlington, MA (US)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 493 days.

(21) Appl. No.: 14/493,892

(22) Filed: Sep. 23, 2014

(65) Prior Publication Data

US 2016/0084777 A1    Mar. 24, 2016

(51) Int. Cl.
*G01N 23/22* (2006.01)
*G01N 23/223* (2006.01)

(52) U.S. Cl.
CPC ..... *G01N 23/223* (2013.01); *G01N 2223/076* (2013.01); *G01N 2223/301* (2013.01); *G01N 2223/303* (2013.01)

(58) Field of Classification Search
CPC .... A61B 6/4405; A61B 6/4411; G01N 23/20; G01N 23/20008; G01N 23/20025; G01N 23/22; G01N 23/2204; G01N 23/223; G01N 2223/05; G01N 2223/06; G01N 2223/07; G01N 2223/076; G01N 2223/30; G01N 2223/301; G01N 2223/303; G01N 2223/308; G01N 2223/309; G01N 2223/34; G01V 5/0016; G01V 5/0025; G01V 5/0041; G21K 5/00; G21K 5/04; G21K 5/08
See application file for complete search history.

(56) References Cited

U.S. PATENT DOCUMENTS

| | | | | |
|---|---|---|---|---|
| 3,399,303 A | * | 8/1968 | Sigmund | G01N 23/203 250/308 |
| 4,450,576 A | * | 5/1984 | Lubecki | G01N 23/223 378/47 |
| 7,939,450 B2 | | 5/2011 | Yamashita et al. | |
| 2012/0294418 A1 | | 11/2012 | Yellepeddi et al. | |
| 2014/0204337 A1 | | 7/2014 | Kulkarni et al. | |
| 2016/0084777 A1 | * | 3/2016 | Smith, Jr. | G01N 23/223 378/45 |

FOREIGN PATENT DOCUMENTS

| | | | | | |
|---|---|---|---|---|---|
| JP | 56060337 A | * | 5/1981 | | G01N 23/223 |
| JP | 06338660 B2 | * | 8/1988 | | G01N 23/223 |

* cited by examiner

*Primary Examiner* — Thomas R Artman
(74) *Attorney, Agent, or Firm* — C. Tricia Liu

(57) ABSTRACT

Disclosed is an attachable spacer applied to the front base plate of a hand-held and self-contained XRF testing device that holds the face plate at a forwards tilt towards a test sample, and ensures that only the top rim of the face plate ever touches a test sample. The resulting triangular gap minimizes contact between the front plate window and the test surface, prevents the transfer of heat to the XRF testing device's circuitry, and locks in a fixed distance between the face plate of the XRF testing device and the sample being tested.

18 Claims, 4 Drawing Sheets

SPACER ACCESSORY FOR XRF HANDHELD ANALYZERS

FIELD OF THE INVENTION

This invention relates to X-Ray Fluorescence (XRF) portable instruments configured to inspect, test and analyzing elemental composition of a test object, more particularly to a spacer accessory to be attached to the instruments.

BACKGROUND OF THE INVENTION

There are many non-destructive testing and/or XRF analysis applications involving complex situations which require thickness measurement, corrosion inspection and chemical composition analysis on high temperature test objects. As an example, sulfide corrosion of oil pipes is a significant cause of leaks and issues for the refining industry that cause early replacements, unplanned outages, loss of property, and, in extreme cases, injury to workers. According to the American Petroleum Institute (API) Recommended Practice 939-C (Guidelines for Avoiding Sulfidation Corrosion Failures in Oil Refineries), ⅓ of all high temperature sulfidic corrosion failures are due to low silicon content in the piping. The inspection of a pipe's corrosion status, chemical composition would require conducting XRF analysis on high temperature pipes.

Elemental analysis of oil refinery pipes with handheld, self-contained X-Ray Fluorescence (XRF) devices is a preferred method to help predict and prevent pipe failures from occurring. These handheld devices typically have a front plate window whereby an X-ray is emitted out to a test object, and the responding energy returning from the test object enters back to a detector in the device. On regular test objects of which high temperature is not present, the devices are usually held by operators in such a way that the front plate touches the surface of the test object.

However when the test object is of high temperature during an XRF operation, existing XRF device designs present problems as to how the operator can hold the handheld so that the front plate window can be placed in relation to the test object in the desirable manner. First, if the front-plate window touches the surface of the test object being tested, the front plate window might sustain damage or too much heat is trapped between the front plate and the test object. And high temperature oil pipes might contaminate the window, invalidating the result. Therefore some gap between the front plate window and the testing surface is desirable. Second, if the gap between the front-plate and the sample is too great, not enough X-ray energized energy from the sample is captured during the test for the analyzer, and the result is too faint to be accurate. Lastly, if the gap between the front-plate window and the sample being tested wobbles and is inconsistent, the air from the varying gaps attenuates the X-Rays inconsistently (more so for lighter elements such as silicon), and distorts the test results of the sample.

U.S. Pat. No. 7,939,450 B2 discloses an apparatus and method for processing a substrate with silicon to control spaces between the layers, and eliminate damage to transistor structures. While this method optimally automates the placement of layer spacing (and prevents the transfer of heat from the material), the solution does not solve the risk of potential damage to a front plate window.

U.S. Pat. No. 2012/0294418 A1 discloses a method of using a goniometer in order to rotate a testing sample to a precise angular position for XRF analysis. This solution though does not minimize the risk of contamination of the front-plate, nor does it allow an air flow that creates a gap which prevents heat from being transferred from the sample to the XRF analyzer.

U.S. Pat. No. 2014/0204377 A1 discloses an auto-calibration, auto-clean, and auto-focus functionality for spectroscopic instruments (including XRF test devices) from a controller that configures motors to move an optics stage and a laser, in order to protect a front plate window. However, this solution is heavily dependent on software operation, and does not have the practicality of a simpler mechanical solution.

An inexpensive, easy to set up solution that can save the display window of an XRF device from abrasion and contamination, yet maintain a close and steady distance from a sample being tested, would be of great economic and ergonomic value. It would speed up XRF testing, reduce equipment replacement on a portable XRF testing device, and retain a higher percentage of valid test samples.

SUMMARY OF THE INVENTION

Disclosed is an attachable and removable spacer applied to the front base plate of a hand-held and self-contained XRF testing device that holds the face plate at a forwards slight tilt towards a test sample. The usage of such spacer allows only the top rim of the face plate and the spacer touch a test sample. The resulting triangular gap minimizes contact between the front plate window and the test surface, prevents the transfer of heat from the test object to the analyzer, and maintains a fixed distance between the face plate of the XRF testing device and the sample being tested.

BRIEF DESCRIPTION OF THE OF THE DRAWINGS

Figure 4A:
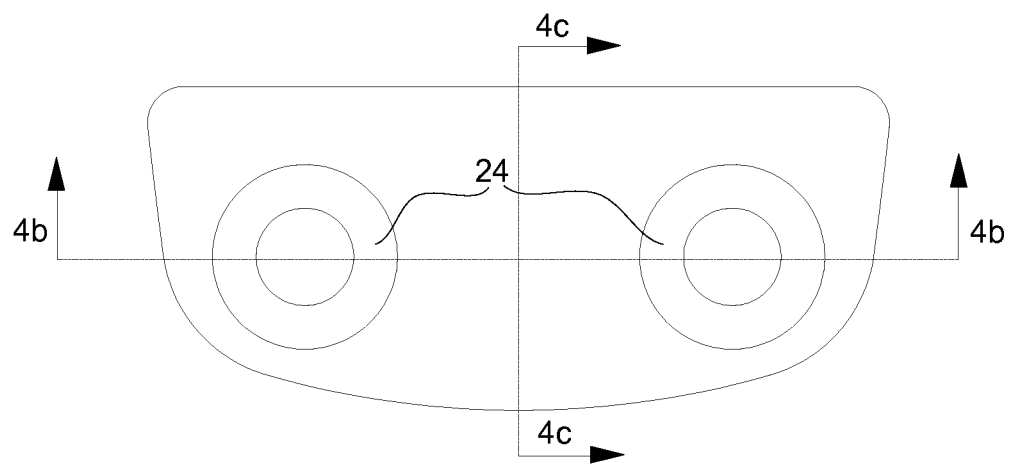
Figure 4B:
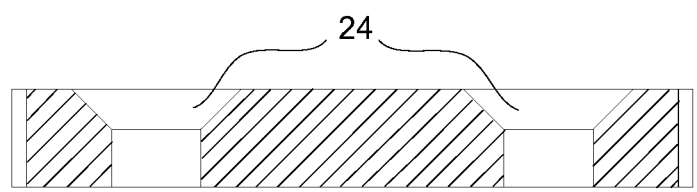
Figure 4C:
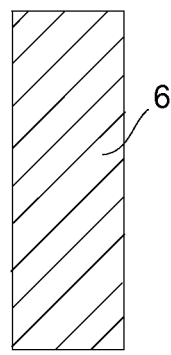

FIGS. 4a, 4b, and 4c are views of the spacer design in top and cross sectional views.

DETAILED DESCRIPTION OF THE INVENTION

The preferred embodiment of an XRF instrument creating a consistent space between the front window and the test object is herein presented by referring to FIGS. 1-4d.

Figure 1:
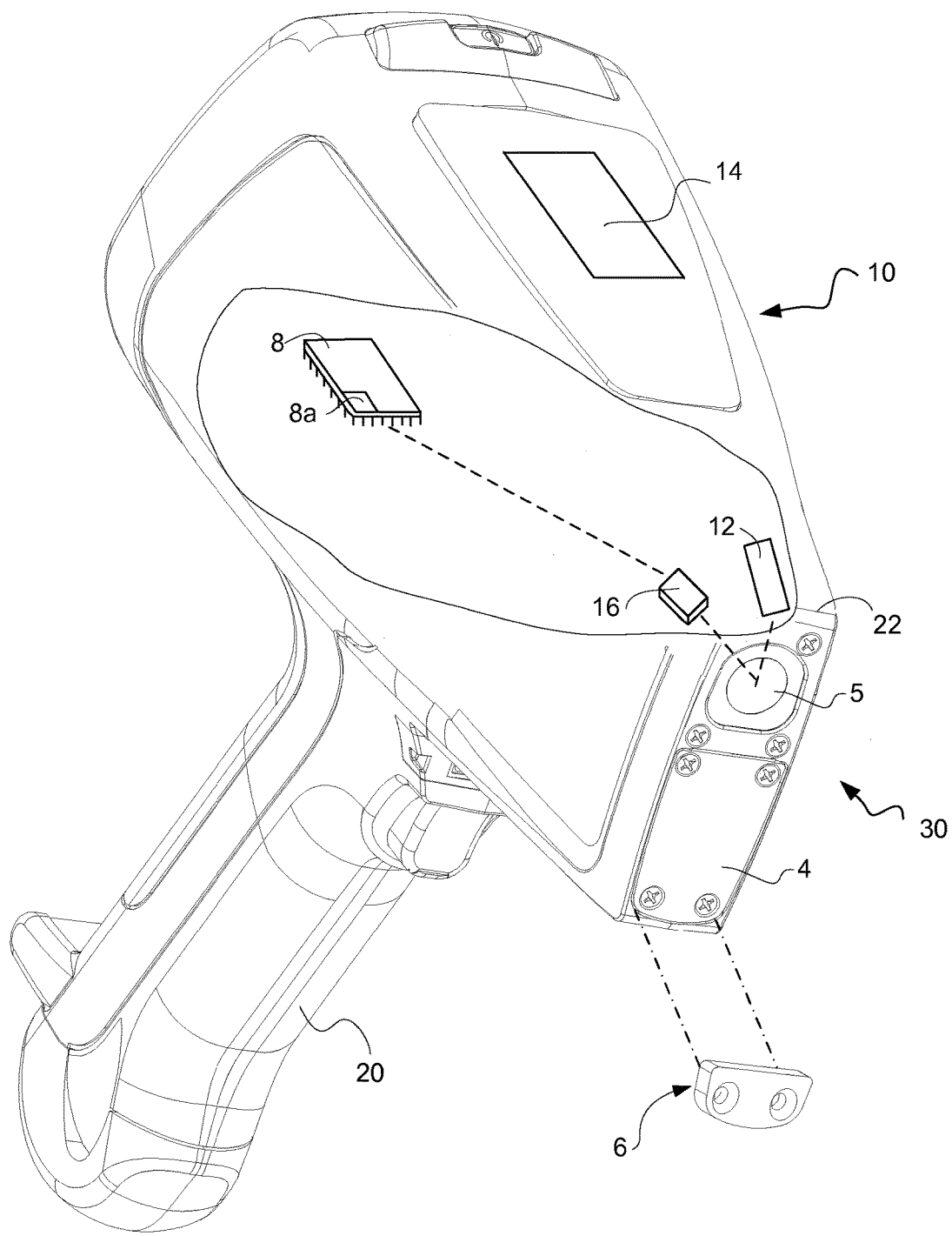
FIG. 1 is a schematic of an XRF instrument with a removable spacer ready to be attached the base plate of the XRF instrument according to the present disclosure.

Referring to FIG. 1, a conceptual view of an XRF instrument 10 is configured to couple with a spacer 6, one at a time during operation. The XRF instrument further optionally includes an X-ray source 12, a detector 16, a data processor and memory 8, a display 14, and a front plate window 5 largely in the same way as conventional XRF instruments.

A front base plate 4 is devised as in conventional XRF instruments. An important novel aspect of the solution herein presented includes the employment of spacer 6, with which any number can be attached over front base plate 4 according to the present invention.

An immediate exemplary usage of such an embodiment is to affix spacer 6 to front base plate 4 in semi-removable fashion, such as using screws. During operation, the instrument is held by an operator at handle 20, with one edge of the front plate 22 and part of spaces 6 come into contact with the surface of the test object. With spacer 6 attached to base plate 5, a consistent distance between front plate window 5 and the testing sample is formed. This is particularly important for elements with lower atomic numbers such as samples of silicon. At the meanwhile, the gap between testing surface and front plate window 5 created by space 6 decrease the heat trapped under the front plate window 5 and front base plate 4, creating a significant benefit avoiding excess heat to be transferred into the instrument.

Reference is still made to FIG. 1. Spacer 6 is preferably attached over front base plate 4 by using a removable attaching means. Accordingly, spacer 6 is shown to be configured to be attached to front base plate 4 using two screws. Alternatively, spacer 6 can be attached by removably attaching means, which should be within the scope of the present disclosure.

Alternatively, any number of spacers 6 can be used depending on the application. For low atomic numbers of test samples, large air attenuation is not desirable. Therefore, no additional spacer 6 is needed for such situation. It should be appreciated that the usage of any number of, and any combination of any kinds of spacers, collectively numerated as 6 in FIGS. 1 and 2 should be determined by the testing specifics, and the usage of all such should be within the scope of the present disclosure.

Figure 2A:
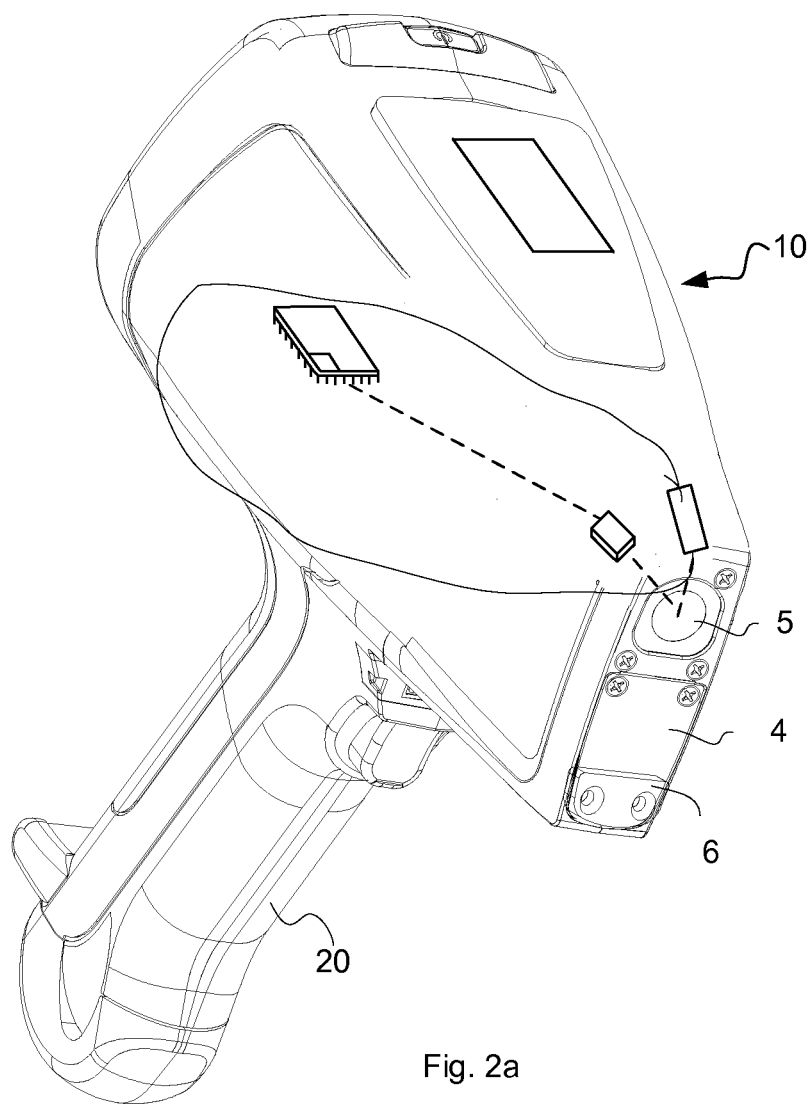
FIGS. 2a and 2b are schematics of the XRF instrument with the removable spacer attached on the base plate.

Further as shown in FIG. 1 and FIG. 2a, in this preferred embodiment, the screw holes on spacer 6 are of the same size as, and aligned with, the existing screw holes of front base plate 4. In this way, spacer 6 shares the same set of screws as the existing front base plate 4. This is to simplify the design modification and the operation of adding and/or removing spacer 6.

Referring to FIG. 2a, XRF instrument 10 is conceptually shown when spacer 6 is attached onto front base plate 4.

Figure 2B:
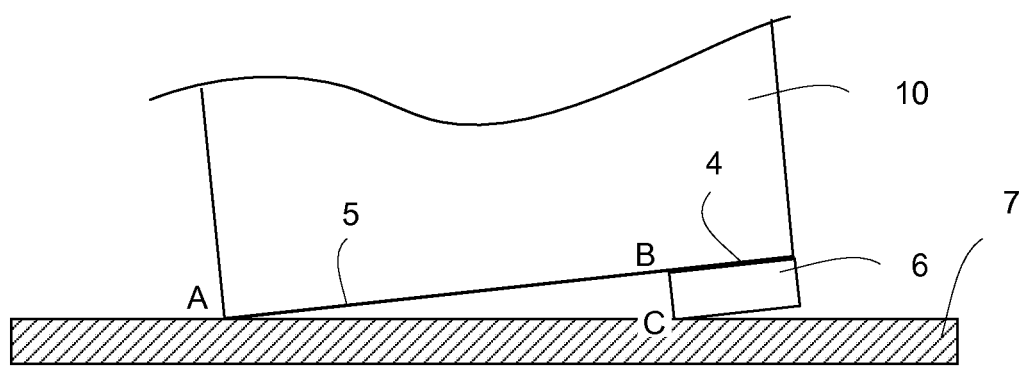

Referring to FIG. 2b, with spacer 6 attached, the only contact points are A on the rim of instrument 10 and B on spacer 6. The gap in a shape of triangle ABC creates a space to avoid direct contamination of window 5. The minimum contacting surface helps avoid heat from test object 7 being directly conducted into instrument 10.

Alternatively, any other removably attaching means of spacer 6 is within the scope of the present disclosure. Such attaching means may include the usage of latch, pressure fitting, etc.

It should be noted that the preferred material of space 6 would be of low thermal conductance so that heat from the test object is not easily conducted into the instrument. Materials suitable for spacer 6 include ceramic, which is a primary material of choice.

Figures 3A, 3B:
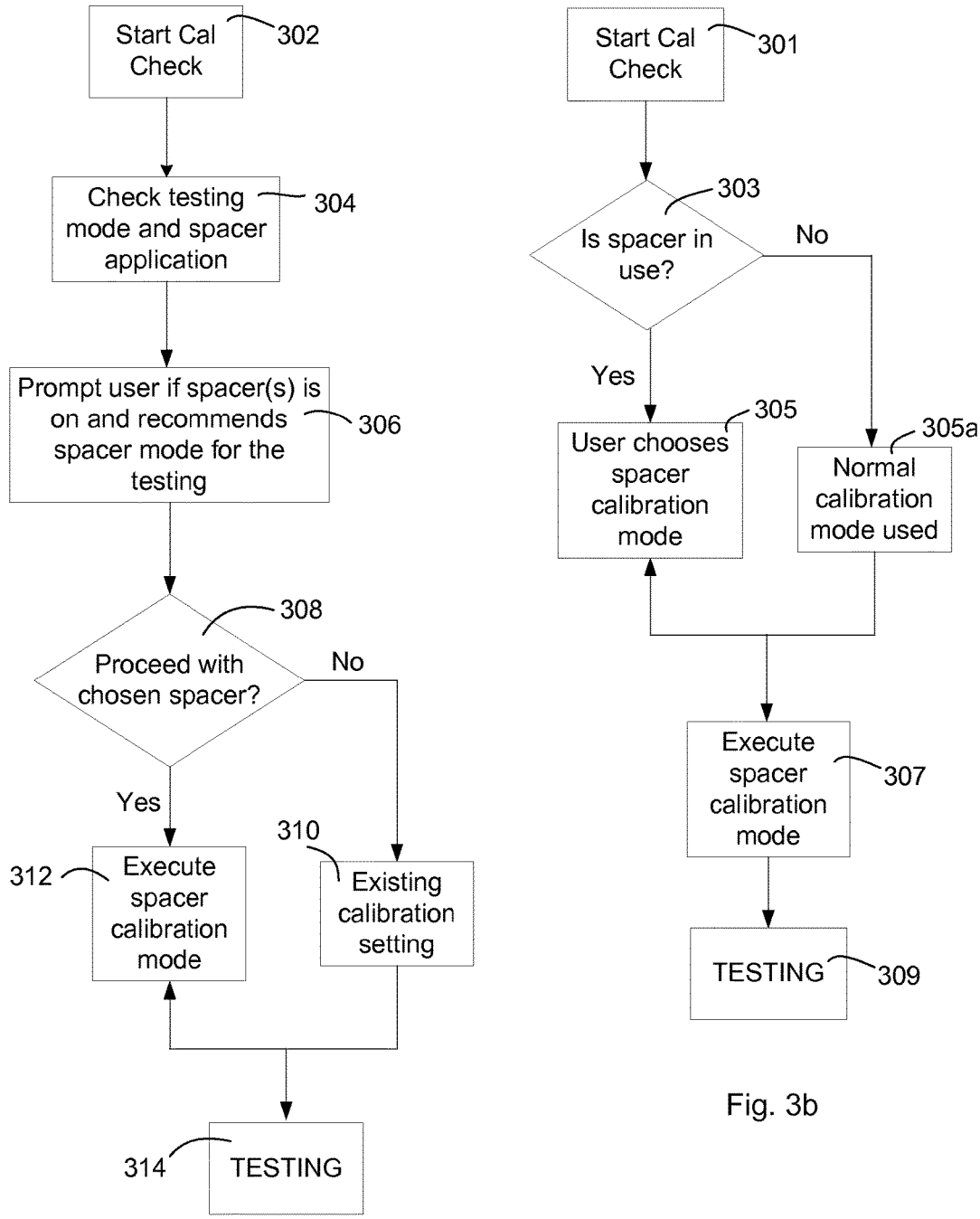
FIGS. 3a and 3b are flowcharts of the process for operating the XRF instrument accommodating the application of the spacer.

Reference is now primarily made to FIG. 3a with continued reference to FIG. 1. FIG. 3 is a flowchart showing an operational procedure related to the usage of the embodiment shown in FIG. 1.

In order to accommodate the usage of a plurality of removable spacers according to the present invention, XRF instrument 10 is preferably devised with a plurality of corresponding calibration modes, factory-preloaded onto data processor and memory 8, according the factory calibration when corresponding spacer is used.

It should be noted that the different calibration modes for different types of removable spacers 6 can be either designed in a new XRF instrument, or achieved by modifying an existing calibration module or functional block residing on the processor of an existing XRF product. The modified calibration module is shown in FIG. 1 as 8a. It can also alternatively be calibrated in a field operation or in a manufacturing set up, all of which should be within the scope of the present invention.

Continuing with FIG. 3a, the method of calibrating an XRF instrument for a specific spacer is commonly known. Different calibration modes can be achieved in manufacturing settings for different types of the spacers.

Alternatively, if the thickness of the spacers is substantially homogenous and standardized, one can populate the values of different calibration modes by calculating the energy-dependent effect on the spectrum caused by the corresponding spacer. One can conduct sufficient number of calibration runs for a specific spacer, which yields a calibration factor for the spacer by comparing to the energy reading of the same XRF instrument without the spacer applied on the same set of samples.

Another note on the calibration modes is that it is preferable to prepare all possible calibration modes with corresponding calibration values for all possible combinations of using, or without using, any and any number of spacers provided with the instrument. The calibration values are stored in data processor and memory 8.

The calibration modes is preferably made in a form of an executable functional code associated with corresponding calibration values store in, and as a module herein named calibration module 8a shown in FIG. 1. The calibration procedure preferably includes steps as follows.

Continuing with FIG. 3a, in step 302, the user starts testing by starting a calibration check with a calibration mode mostly used for a previous session of testing, i.e. for a light element or heavy atomic element. "Cal check" is commonly referred in XRF as shooting a sample of a known elemental composition.

In step 304, calibration module 8a checks from a calibration shot on a calibration sample to determine whether the spacer is applied, and to determine automatically what kind of spacer is applied on front base plate 4. Alternatively, when the known kind of element for testing (example: Si) is provided to the instrument, module 8a can be configured to determine if spacer 6 is the right match for such testing, noting that a lower atomic number needs a thinner spacer. Alternative step 304 can be that calibration module 8a only checks if spacer 6 is applied or not, and prompts the user to check if spacer 6 is the intended kind of spacer to be attached.

It can be understood by those skilled in the art that after the calibration check is initiated at step 302, the energy reading on the known sample can indicate if spacer 6 is applied. And by comparing the known calibration factors stored in the instrument, optionally the calibration module 8a can yield what kind of spacer is presently attached to the front base plate.

Continuing with FIG. 3a, in step 306, calibration module 8a prompts the user via display 14 whether spacer 6 is applied, what kind of spacer is applied on front base plate 4, and whether to change or remove spacer 6, or alternatively change the calibration mode.

In step 308, module 8a further checks which spacer (or no spacer) is chosen by the user. If a specific spacer is chosen, the procedure moves onto step 312. If no spacer is chosen, the procedure moves onto step 310. In step 412, a specific calibration mode suited for the chosen spacer is chosen by calibration module 8a, and executed by XRF instrument 10. Alternatively, the user can also choose the calibration mode via display 14.

In step 310, if the user determines not to use any spacer and remove the same, the existing calibration mode for front base plate 4 without spacer 6 is executed to calibrate instrument 10. In step 312, XRF instrument 10 is ready for testing, which occurs in step 314.

Reference is now made to FIG. 3b with continued reference to FIG. 1, where alternatively a user can calibrate XRF instrument 10 manually. In step 301, the user starts a "cal check" test. In step 303, if it is needed to choose a cal mode for spacer. If the user knows a spacer is attached, the user enters "yes". Otherwise the user enters "No", and the procedure moves onto step 305a. Upon choosing "yes", in step 305 the user enters a calibration mode corresponding to the specifically know spacer that is attached. In step 307, the chosen cal mode corresponding to the spacer is executed. The instrument is then ready for testing with the specific spacer on in step 309.

Reference is now made to FIGS. 4a, 4b and 4c, and continuously to FIG. 1, where more details of the preferred embodiment of spacer 6 are provided. Referring to FIG. 4a, which is a top view of spacer 6, screw holes 24 are preferably aligned with those of front base plate 4. The size, contour and shape of spacer 6 should also be very close to the corresponding part of front base plate 4. Cross-sectional views FIGS. 4b and 4c also exhibit the screw holes and the design of spacer 6. The thickness of spacer 6 exhibited in FIGS. 4b and 4c is exemplary and variations in thickness are within the scope of the present disclosure.

In addition to screws used in FIGS. 4a, 4b and 4c, it should be understood by those skilled in the art that other means can be used instead to attach and re-attach spacer 6 onto front base plate 4 of XRF instrument 10 (as well as their associated usage of corresponding calibration modes), and should all be within the scope of the present disclosure.

What is claimed is:

1. An X-Ray Florescence (XRF) test system comprises an XRF test instrument used for testing a test object's responses to X-rays, the instrument comprising a front face configured to be placed facing the test object, the front face including a front base plate and a test window through which the X-rays and its responsive energy is allowed to pass through, wherein the front face and the window are substantially in the same plane,
   the system further comprising at least one spacer to be attached to or be part of the front face to create a constant space between the front face and the test object when the front face is put against the test object, and,
   wherein the test instrument further comprises an X-ray source, an X-ray detector, and a data processor and memory, the data processor and memory further comprising a calibration module including at least two calibration modes, of which the first mode corresponds to the operational status of the instrument without the spacer being applied onto the front base plate, and the second mode corresponds to the operational status of the instrument with the spacer applied onto the front base plate.

2. The system of claim 1, wherein the front base plate abuts the window and is in the same plane with the window.

3. The system of claim 2, wherein the spacer is configured to be attached to the front base plate in a fashion to be removed from or attached or re-attached over the front base plate.

4. The system of claim 2 wherein the at least one spacer is configured to be removably attached to the front base plate along or partially along the circumference of at least one front base plate.

5. The system of claim 3, wherein the at least one spacer is configured to be removably attached to the front base plate by screws along or partially along the circumference of at least one front base plate.

6. The system of claim 1 wherein the at least one spacer is configured to be removably attached to the front base plate by pressure fitting along or partially along the circumference of at least one front base plate.

7. The system of claim 1, wherein the calibration modes correspond to the calibration values obtained for different numbers and different kinds of the spacer being attached to the front base plate.

8. The system of claim 7, wherein the calibration values for a specific one of the at least one spacer is obtained from calibration procedures on the XRF instrument with the specific one of the at least one spacer attached.

9. The system of claim 8, wherein the calibration values for a specific one of the at least one spacer is calculated by applying the calibration value of the first mode with a corresponding calibration factor specific to the specific one of the at least one spacer.

10. The system of claim 9, wherein the calibration factor is obtained by comparing the calibration values obtained with and without the specific one of the at least one spacer applied.

11. The system of claim 1, wherein the spacer calibration modes encompass the entire or any part of possibilities under which any and any number of the at least one spacer is applied to the front base plate.

12. The system of claim 1, wherein the data processor and memory is configured, during a calibration session, to execute the steps including:
   prompting the user whether and how many of the at least one spacer calibration mode is currently applied, and recommending which of the at least one spacer calibration mode should be applied,
   confirming which of the at least one, or none, of the spacer calibration mode is being used for the present testing,
   selecting the first or the second spacer calibration mode according to the spacer mode applied, and
   calibrating and readying the XRF instrument for testing.

13. The system of claim 12, wherein the steps further including identifying which kind and how many of the at least one spacer are applied.

14. The system of claim 12, wherein the steps further including providing checking and identifying whether the identified spacer is a good match to the test as tasked.

15. The system of claim 12, wherein the steps further including prompting the user when the identified spacer application is not a good match with the test as tasked.

16. A method of providing at least one spacer to be attached to or to be part of a front face of an XRF instrument used for testing a test object's responses to X-rays, the instrument comprising a front face configured to be placed facing the test object, the front face including a front base plate and a test window through which the X-rays and its responsive energy is allowed to pass through,
   wherein the front face and the window are substantially in the same plane, wherein the at least one spacer is to create a constant space between the front face and the test object when the front face is placed against the test object, and, wherein the instrument has at least two calibration modes, of which the first mode corresponds to the operational status of the instrument without the spacer being applied onto the front base plate, and the second mode corresponds to the operational status of the instrument with the spacer applied onto the front base plate.

17. The method of claim 16, wherein the front base plate abuts the window and is in the same plane with the window.

18. The method of claim 17, wherein the spacer is configured to be attached to the front base plate in a fashion to be removed from or attached or re-attached over the front base plate.

\* \* \* \* \*